United States Patent
Hallen (10) Patent No.: US 12,357,504 B2
(45) Date of Patent: Jul. 15, 2025

(54) AEROSOL MITIGATION COLLAR FOR OPHTHALMIC PROCEDURES

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 947 days.

(21) Appl. No.: 17/370,017

(22) Filed: Jul. 8, 2021

(65) Prior Publication Data

US 2022/0015946 A1 Jan. 20, 2022

Related U.S. Application Data

(60) Provisional application No. 63/052,053, filed on Jul. 15, 2020.

(51) Int. Cl.
*A61F 9/007* (2006.01)
*A61M 3/02* (2006.01)

(52) U.S. Cl.
CPC ....... *A61F 9/00745* (2013.01); *A61M 3/0279* (2013.01); *A61M 2210/0612* (2013.01)

(58) Field of Classification Search
CPC .... A61F 9/0026; A61F 9/007; A61F 9/00736; A61F 9/00745; A61F 2009/0052; A61M 3/0279; A61M 2210/0612; A61M 11/00; A61M 25/0067; A62M 25/0067
USPC ........................................................ 606/107
See application file for complete search history.

(56) References Cited

U.S. PATENT DOCUMENTS

| | | | | |
|---|---|---|---|---|
| 4,381,007 A | * | 4/1983 | Doss | A61B 18/14 606/50 |
| 5,112,300 A | | 5/1992 | Ureche | |
| 5,645,530 A | * | 7/1997 | Boukhny | A61F 9/00745 606/107 |
| 5,735,833 A | * | 4/1998 | Olson | A61M 35/00 604/289 |
| 2012/0172874 A1 | * | 7/2012 | Fischer | A61B 18/042 606/49 |
| 2015/0112376 A1 | * | 4/2015 | Molaei | A61B 17/221 606/200 |
| 2017/0224283 A1 | * | 8/2017 | Kassab | A61B 5/0538 |

(Continued)

FOREIGN PATENT DOCUMENTS

| | | |
|---|---|---|
| JP | 3110910 U | 7/2005 |
| WO | 0117589 A1 | 3/2001 |

(Continued)

OTHER PUBLICATIONS

Text from WO 2006089611 (Year: 2006).*

(Continued)

*Primary Examiner* — Kankindi Rwego (74) *Attorney, Agent, or Firm* — PATTERSON + SHERIDAN, LLP (57) ABSTRACT

An ophthalmic surgical instrument system includes an ophthalmic instrument that includes a shaft and a lumen extending through the shaft. A sleeve that has a tubular body portion that receives and surrounds the ophthalmic instrument. An annulus is defined between the ophthalmic instrument and the sleeve. An aerosol mitigation collar extends from the sleeve. The aerosol mitigation collar includes a tubular section and a skirt extending outwardly and distally from the tubular section.

20 Claims, 10 Drawing Sheets

(56) References Cited

U.S. PATENT DOCUMENTS

2020/0069913 A1  3/2020  Lenneman et al.

FOREIGN PATENT DOCUMENTS

| WO | WO-2006089611 A1 * | 8/2006 | ............. A61F 9/007 |
| WO | 2007087061 A2 | 8/2007 | |

OTHER PUBLICATIONS

Darcy Kieren et al : "Reducing visible aerosol generation during phacoemulsification in the era of Covid-19", Eye, Nature Publishing Group, GB, vol. 35, No. 5, pp. 1405-1410, Jun. 26, 2020, DOI: 10.1038/S41433-020-1053-3.

* cited by examiner

```
           ┌─────────────┐
           │    Start    │─602
           └──────┬──────┘
                  ▼
  ┌───────────────────────────────────┐
  │ Couple aerosol mitigation collar to sleeve │─604
  └───────────────┬───────────────────┘
                  ▼
  ┌───────────────────────────────────┐
  │    Insert sleeve into patient's eye    │─606
  └───────────────┬───────────────────┘
                  ▼
  ┌───────────────────────────────────┐
  │ Contact aerosal mitigation collar with patient's eye │─608
  └───────────────┬───────────────────┘
                  ▼
  ┌───────────────────────────────────┐
  │ Aerosol mitigation collar blocks release of fluids │─610
  └───────────────┬───────────────────┘
                  ▼
  ┌─────────────────────────────────────────────────────┐
  │ Adjust aerosol mitigation collar to accommodate changes in depth │─612
  └───────────────┬─────────────────────────────────────┘
                  ▼
           ┌─────────────┐
           │     End     │─614
           └─────────────┘
```

AEROSOL MITIGATION COLLAR FOR OPHTHALMIC PROCEDURES

CROSS-REFERENCE TO RELATED APPLICATIONS

This application claims priority to and benefit of U.S. Provisional Patent Application No. 63/052,053, filed Jul. 15, 2020, the entire contents of which are incorporated by reference herein in its entirety

TECHNICAL FIELD

The present disclosure relates generally to methods and systems for performing ophthalmic procedures and more particularly, but not by way of limitation, to a flexible collar for use with an irrigation sleeve for preventing aerosol dispersion of intraocular fluids.

BACKGROUND

This section provides background information to facilitate a better understanding of the various aspects of the disclosure. It should be understood that the statements in this section of this document are to be read in this light, and not as admissions of prior art.

A number of different ophthalmic procedures involve the use of an instrument with an irrigation sleeve that is inserted into the eye for performing all or part of the procedure. For example, ophthalmic phacoemulsification is a procedure commonly used for removal of cataractous lenses. The procedure typically involves insertion of a working tip of an ultrasonic handpiece into the eye. In such handpieces, ultrasonic vibrations drive the working tip, which the physician can maneuver against the cataractous lens in order to break up or emulsify the lens for removal and replacement.

Ultrasonic ophthalmic phacoemulsification handpieces in common use typically are designed not only to drive the ultrasonic working tip but also to perform additional functions, such as to facilitate supply of irrigation fluid into the eye and to facilitate aspiration of irrigation fluid and the fragmented or emulsified lens from the eye. To facilitate the irrigation function, such ultrasonic handpieces may include an irrigation sleeve around the working tip for directing the irrigation fluid. The handpiece may be connected to a control console by one or more electric cables and flexible tubes. The electric cable supplies power to the components for driving vibration of the working tip, while the tubes serve as conduits for the irrigation fluid supplied to the eye and for the aspirated fluid drawn from the eye.

A number of different ultrasonic handpieces and working tips have been proposed and used.

In addition to ultrasonic phacoemulsification, other ophthalmic procedures may be performed in which an instrument with an irrigation sleeve is inserted into the eye for performing all or part of the procedure. The irrigation sleeve may be placed around the working tip of the instrument so that the distal end of the working tip of the instrument extends through a distal opening in the end of the irrigation sleeve. Irrigation occurs by delivering irrigation fluid through the sleeve, which exits through a relatively large circular side opening proximate the distal end of the irrigation sleeve.

Current irrigation sleeves may be susceptible to an escape of intraocular fluids in aerosol form from the surgical site. Such fluids are capable of carrying infectious pathogens and may put the surgeon and surgical team at risk of exposure and infection.

SUMMARY

Aspects of the disclosure relate to an ophthalmic surgical instrument system. The ophthalmic surgical instrument system includes an ophthalmic instrument that includes a shaft and a lumen extending through the shaft. A sleeve that has a tubular body portion that receives and surrounds the ophthalmic instrument. An annulus is defined between the ophthalmic instrument and the sleeve. An aerosol mitigation collar extends from the sleeve. The aerosol mitigation collar includes a tubular section and a skirt extending outwardly and distally from the tubular section.

Aspects of the disclosure relate to an aerosol mitigation collar. A tubular section receives a portion of a sleeve. A skirt extends outwardly and distally from the tubular section. A contact surface is disposed at a distal end of the skirt. A plurality of pleats are formed in the skirt. The plurality of pleats facilitate compression and expansion of the aerosol mitigation collar.

Aspects of the disclosure relate to a method of containing aerosol fluids during ophthalmic procedures. The method includes coupling an aerosol mitigation collar to a sleeve. A contact surface of the aerosol mitigation collar is contacted with an exterior surface of an eye during an ophthalmic procedure. The aerosol mitigation collar blocks release of aerosol fluids from the eye. A depth of the sleeve within the eye is adjusted while maintaining contact between the contact surface and the eye.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

DETAILED DESCRIPTION

Various embodiments will now be described more fully with reference to the accompanying drawings. The disclosure may, however, be embodied in many different forms and should not be construed as limited to the embodiments set forth herein.

Current irrigation sleeves may be susceptible to escape of intraocular fluids in aerosol form from a surgical site. Such fluids are capable of carrying infectious pathogens and may put the surgeon and surgical team at risk of exposure and infection. Various approaches have been investigated for mitigating the emission of aerosol fluids from the surgical site. These approaches include the use of suction, compressed air directed at the surgical site, reduced incision size, maintaining corneal moisture, and application of a topical gel agent. Most of these approaches have been demonstrated to be ineffective for preventing escape of aerosol fluids from an ophthalmic surgical site. The use of a topical gel agent would prevent escape of aerosol fluids; however, effective use requires frequent re-application.

Figure 1A:
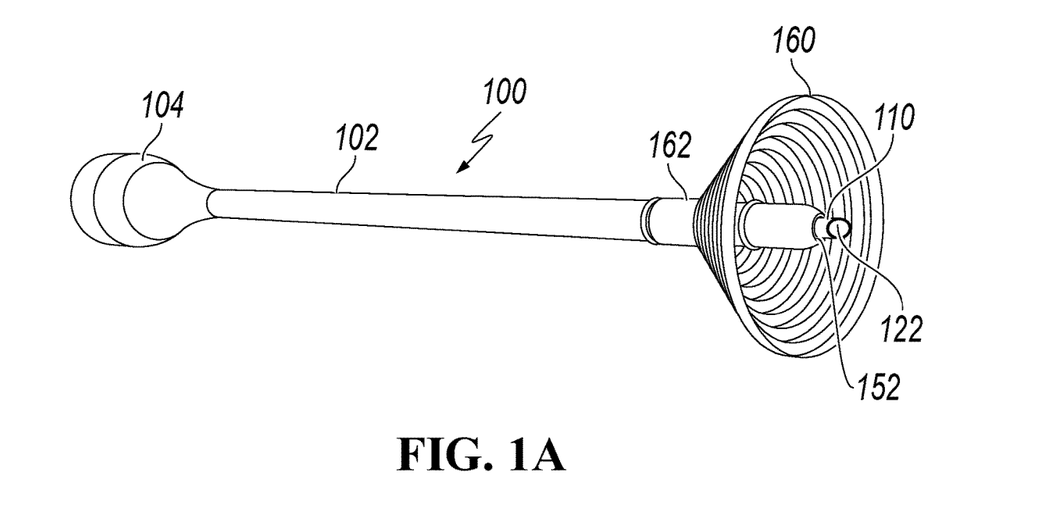
FIG. 1A is a distal perspective view of an ophthalmic instrument inserted into a sleeve and having an aerosol mitigation collar according to aspects of the disclosure.
Figure 1B:
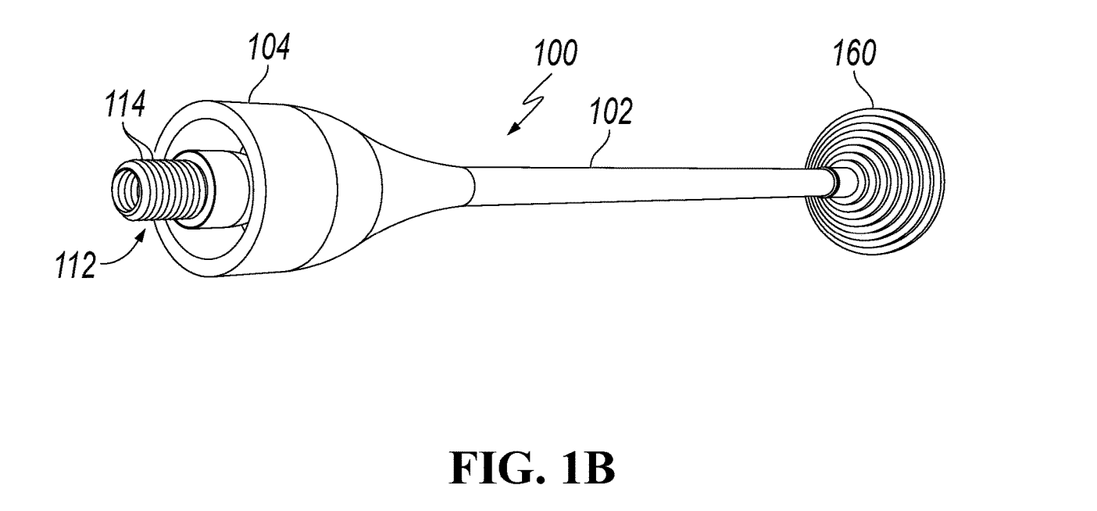
FIG. 1B is a proximal perspective view of the ophthalmic instrument collar of FIG. 1A according to aspects of the disclosure.
Figure 1C:
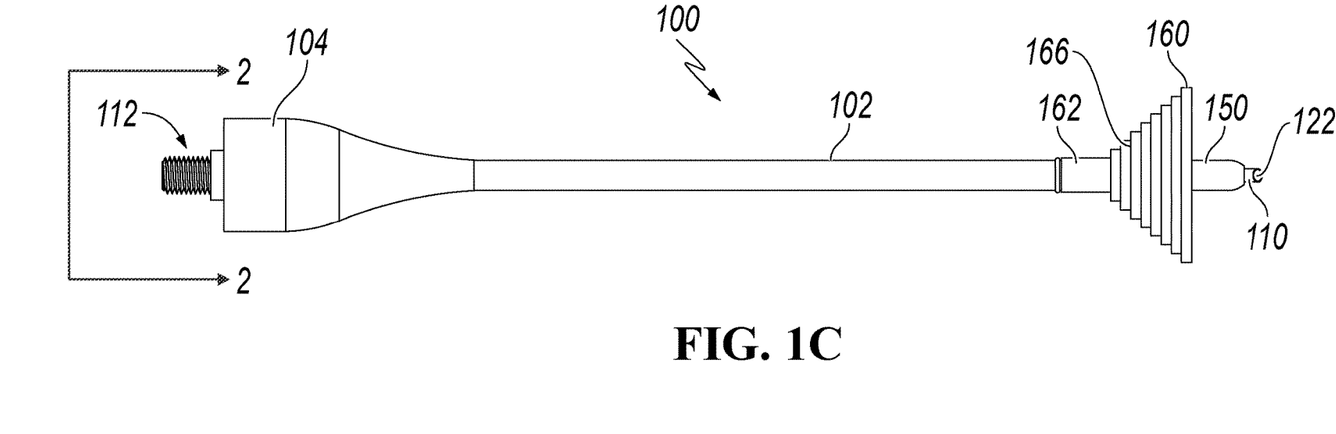
FIG. 1C is a side view of the ophthalmic instrument collar of FIG. 1A according to aspects of the disclosure.
Figure 2:
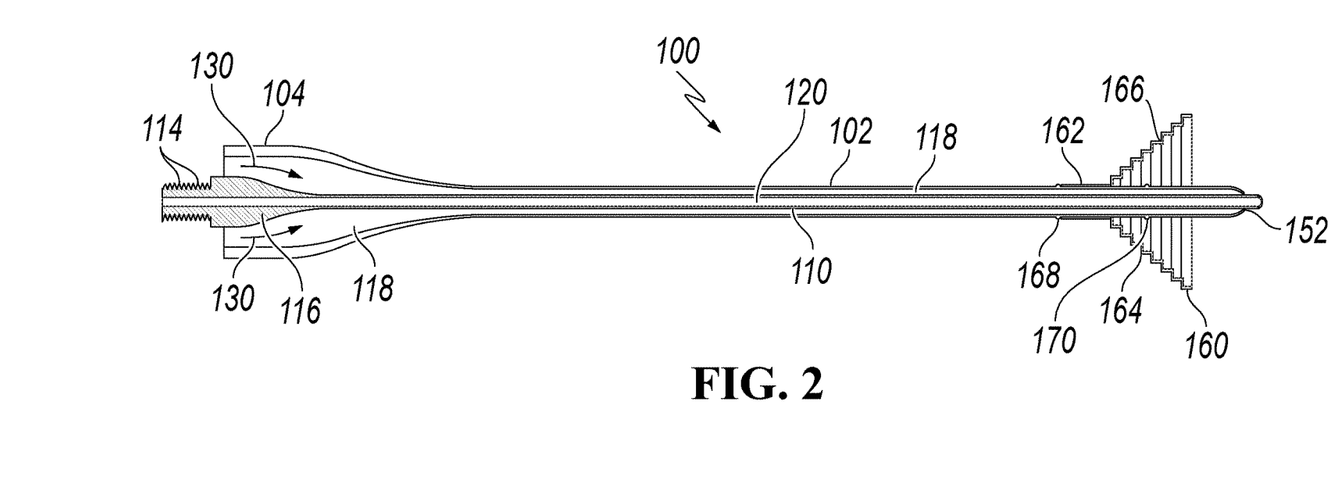
FIG. 2 is a side cross-sectional view of the ophthalmic instrument of FIG. 1C taken along line 2-2 according to aspects of the disclosure.

FIG. 1A is a distal perspective view of an ophthalmic instrument 110 inserted into a sleeve 100 having an aerosol mitigation collar 160. FIG. 1B is a proximal perspective view of the ophthalmic instrument 110 inserted into the sleeve 100 having the aerosol mitigation collar 160. FIG. 1C is a side view of the ophthalmic instrument 110. FIG. 2 is a side cross-sectional view of the ophthalmic instrument 110. For purposes of discussion, the ophthalmic instrument 110 will be described and illustrated herein by way of example as a phacoemulsification needle and the sleeve 100 will likewise be described and illustrated herein by way of example as a phacoemulsification irrigation sleeve. However, one of skill in the art will recognize that principles of the disclosure could be extended to numerous other ophthalmic procedures including, for example, anterior capsule surgery, posterior capsule surgery, retinal surgery, or any other ophthalmic procedure requiring simultaneous irrigation and aspiration of a surgical site. Referring to FIGS. 1A-2, collectively, the sleeve 100 includes an elongated, resilient tubular body portion 102, which is configured to surround all but a distal end of the ophthalmic instrument 110. The distal tip of the ophthalmic instrument 110 extends beyond the distal end of the sleeve 100. The ophthalmic instrument 110 includes a lumen 120 formed therein that defines an opening 122 at the distal end of the ophthalmic instrument 110. The sleeve 100 includes an enlarged section 104 that extends from a proximal end of the tubular body portion 102 and is configured to surround a hub 112 and a flared portion 116 of the ophthalmic instrument 110. In various embodiments, the sleeve 100 may be formed, for example, of silicone, or other pliable, resilient material suitable for use in ophthalmic surgery. In various embodiments, the dimensions of the sleeve 100 may vary to facilitate compatibility with ophthalmic instruments of various sizes. In various embodiments, the sleeve 100 is generally suitable for insertion through a small incision in a patient's eye and provides a smooth, non-sharp surface that contacts the patient's eye. In various embodiments, the sleeve 100 serves to insulate the ophthalmic instrument 110 from eye tissue and to effectively seal the incision during, for example, a phacoemulsification procedure. In various embodiments, the sleeve 100 includes an opening 152 formed at the distal end of the tubular body portion 102. The opening 152 may be adapted to accommodate a portion of the shaft of the ophthalmic instrument 110 extending through the opening 152.

In use, the hub 112 of the ophthalmic instrument 110 is screwed into an instrument handpiece (not shown), using threads 114. The enlarged section 104 of the sleeve 100 also attaches to the instrument handpiece. In various embodiments, the sleeve 100 may attach to the instrument handpiece using, for example, internal threads (not shown) formed inside the enlarged section 104 of the sleeve 100. An annulus 118 is defined between the sleeve 100 and the ophthalmic instrument 110. During use, irrigation fluid is provided to the patient's eye through the annulus 118 in the direction indicated by arrows 130. Thus, irrigation fluid flows through the annulus 118, towards the distal end of the sleeve 100, and in various embodiments exits the apparatus, into the eye, through the opening 152, through one or more conventional irrigation ports (not shown), or both. Irrigation fluid and emulsified lens tissue is aspirated away from the eye, through the lumen 120 within the ophthalmic instrument 110, using a suction force applied through the instrument handpiece.

Still referring to FIGS. 1A-2, an aerosol mitigation collar 160 is coupled to the sleeve 100. In various embodiments, the aerosol mitigation collar 160 is constructed of the same silicone, or other pliable, resilient material suitable used to construct the sleeve 100. In other embodiments, the aerosol mitigation collar 160 may be constructed of a similar material that is compatible with the material of the sleeve 100 and suitable for use during ophthalmic procedures. In some embodiments, aerosol mitigation collar 160 is made of a clear, flexible, low friction material. Use of a clear material allows the surgeon to better visualize the surgical site. Since the opening 122 of the ophthalmic instrument 110 (or in this case, a phacoemulsification needle) is centered on the corneal incision, the maximum diameter of aerosol mitigation collar 160 can be slightly larger than the incision size (for example, less than about 5 mm to less than about 3 mm). Most surgical incisions for phacoemulsification surgery are less than about 2 mm. In such a case, the maximum diameter of the aerosol mitigation collar 160 is about 3 mm.

The aerosol mitigation collar 160 includes a sleeve 162 that is of a generally tubular shape. In one example, the diameter of the sleeve 162 is about 1 mm but can be from about 0.5 mm to about 1.5 mm. A skirt 164 extends outwardly and distally from the sleeve 162 such that a distal end of the skirt 164 is of a diameter greater than a proximal end of the skirt 164. In this example, the distal end of the skirt 164 has a diameter of about 3 mm. While shown in the Figures as a cone, the skirt 164 can have a parabolic shape or a cylindrical shape. A surface of the skirt 164 includes accordion-like pleats 166 thereby allowing the skirt 164 to be stretched in the distal direction or compressed in the proximal direction relative to the sleeve 162. Alternatively, the skirt 164 may be smooth without any pleats 166.

Figure 3A:
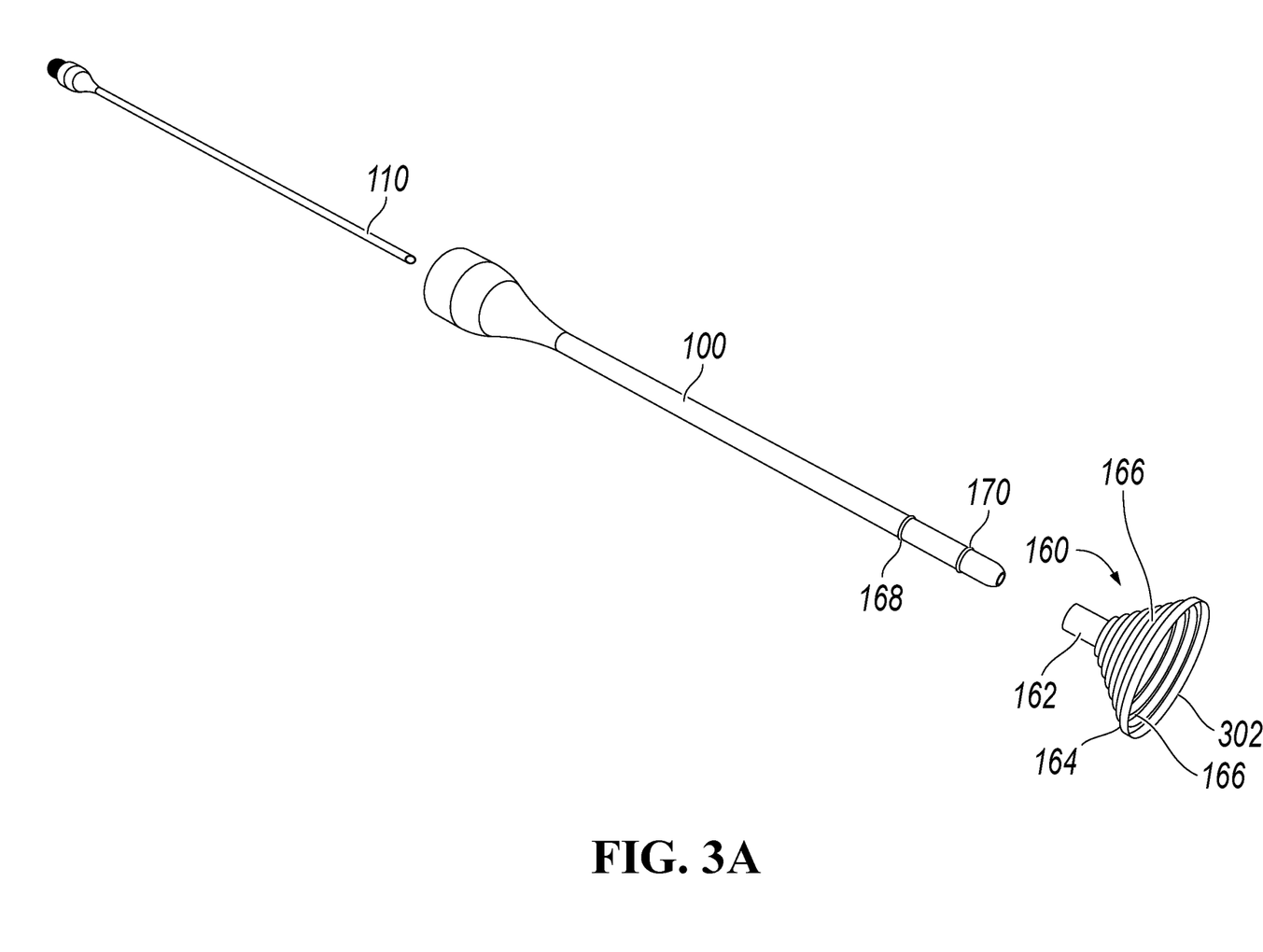
FIG. 3A is an exploded distal perspective view of the ophthalmic instrument of FIG. 1A according to aspects of the disclosure.
Figure 3B:
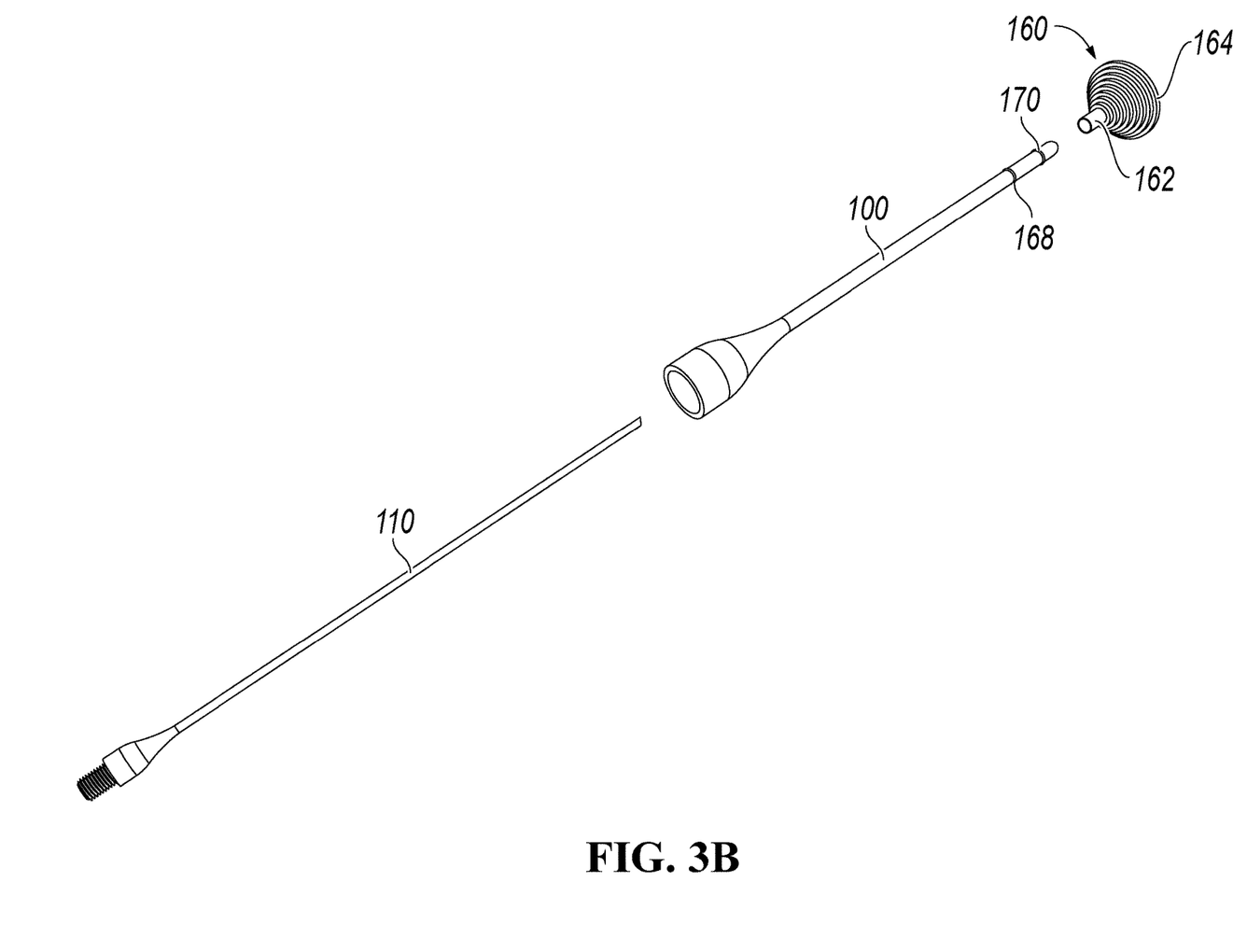
FIG. 3B is an exploded proximal perspective view of the ophthalmic instrument of FIG. 1A according to aspects of the disclosure.

FIG. 3A is an exploded distal perspective view of the ophthalmic instrument 110 showing the sleeve 100 and the aerosol mitigation collar 160. FIG. 3B is an exploded proximal perspective view of the ophthalmic instrument 110 showing the sleeve 100 and the aerosol mitigation collar 160. Referring to FIGS. 3A and 3B collectively, in various embodiments, the sleeve 100 is received into the sleeve 162 such that a friction engagement is formed between the sleeve 162 and the sleeve 100. The engagement between the sleeve 162 and the sleeve 100 prevents inadvertent movement of the aerosol mitigation collar 160 during use and prevents leakage of fluids from the interior of the aerosol mitigation collar 160. While the aerosol mitigation collar 160 is illustrated herein as being removable from the sleeve 100, in other embodiments, the aerosol mitigation collar 160 may be integrally formed with the sleeve 100. As shown in FIG. 3A, a contact surface 302 is formed on a distal end of the skirt 164.

Figure 4:
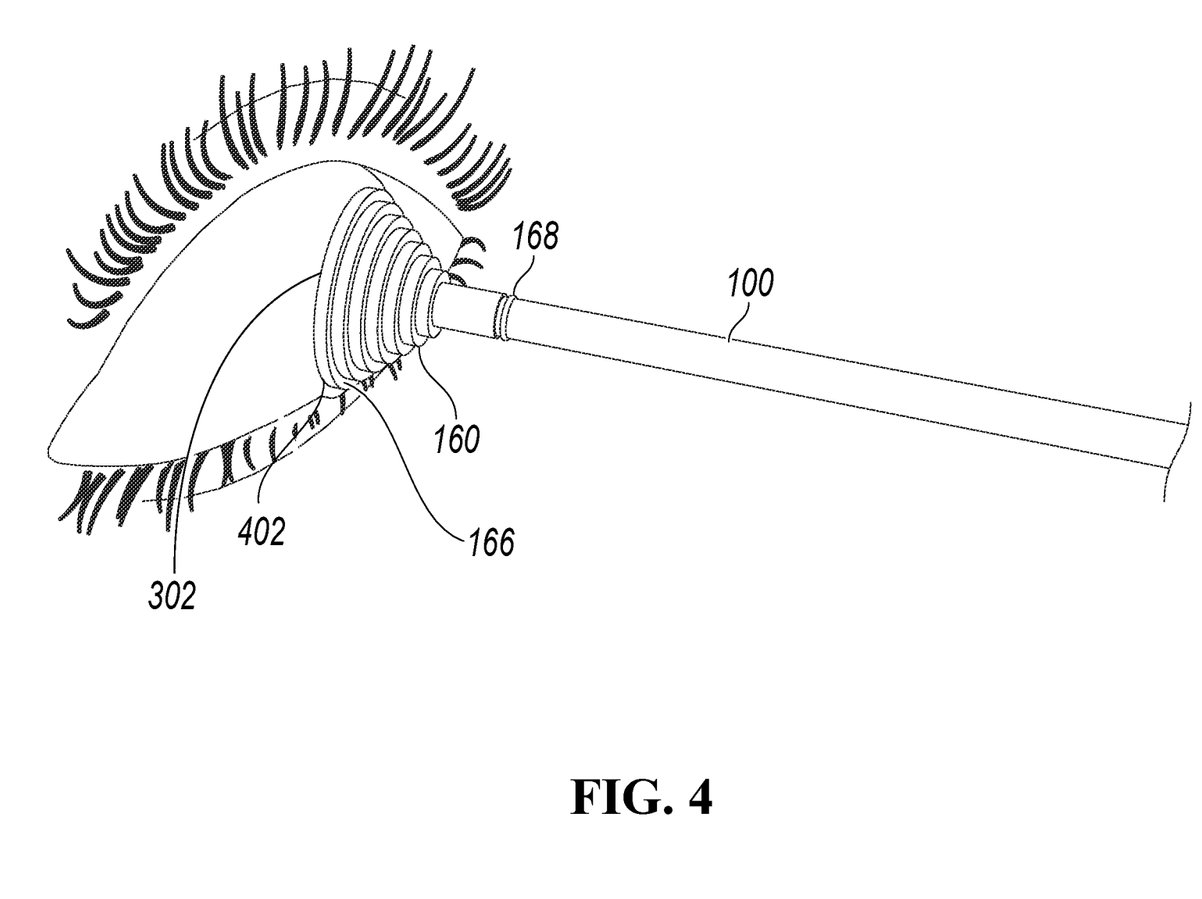
FIG. 4 is a schematic diagram of the ophthalmic instrument of FIG. 1A inserted into an eye according to aspects of the disclosure.

FIG. 4 is a schematic diagram of the ophthalmic instrument 110 inserted into an eye 402. During use, the ophthalmic instrument 110 and the sleeve 100 are inserted into an incision in the eye 402. In the particular case of phacoemulsification, the ophthalmic instrument 110 and the sleeve 100 are inserted into an anterior chamber of the eye 402. The contact surface 302 of the skirt 164 contacts the patient's eye 402. Contact pressure between the skirt 164 and the eye 402 maintains the skirt 164 in contact with the patient's eye 402. During operation, a depth of the ophthalmic instrument 110 and the sleeve 100 may be adjusted many times. The pleats 166 allow the skirt 164 to be compressed as the ophthalmic instrument 110 is inserted deeper into the eye 402. Additionally, the pleats 166 facilitate expansion of the skirt 164 as the ophthalmic instrument 110 is retracted from the eye 402. Thus, the pleats 166 facilitate spring-like movement of the skirt 164. In other embodiments, the sleeve 162 may allow axial movement of the aerosol mitigation collar 160 on the sleeve 100. Thus, as the ophthalmic instrument 110 and the sleeve 100 are inserted into and retracted from the eye 402, the sleeve 162 is able to slide relative to the sleeve 100 in order to accommodate changing depth of the ophthalmic instrument 110 within the eye 402. In such embodiments, the aerosol mitigation collar 160 may slide between a proximal limit 168 and a distal limit 170 (shown in FIGS. 2-3B). In various embodiments, the proximal limit 168 and the distal limit 170 may be formed as, for example, a bump, ridge, or rabbet formed on an exterior surface of the sleeve 100. During operation the proximal limit 168 corresponds to a point of deepest insertion of the sleeve 100 into the eye such as, for example, if the surgeon is treating a posterior aspect of the anterior capsule. The distal limit 170 corresponds to a point of shallowest insertion of the sleeve 100 into the eye such as, for example, during treatment of an anterior aspect of the anterior capsule. In one example, the distance between the proximal limit 168 and the distal limit 170 is equivalent to the circumference of the anterior chamber of a human eye (from 10 to 20 mm).

The opening 122 of the ophthalmic instrument 110 is inserted into the eye through an incision ion the cornea (in the case of phacoemulsification or cataract removal surgery). The contact surface 302 of the areosol mitigation collar 160 rests on the surface of the eye. The opening 122 is moved in the anterior chamber while the contact surface 302 of the areosol mitigation collar 160 rests on the surface of the eye. Accordingly, the areosol mitigation collar 160 deforms as the opening 122 is moved in the eye. Still referring to FIG. 4, the aerosol mitigation collar 160 provides a physical barrier against the escape of aerosolized irrigation fluid, emulsified lens tissue, and intra-ocular fluid. Such a barrier prevents a surgeon and other medical technicians from contacting aerosolized fluids and prevents possible exposure to infectious pathogens. The length of the areosol mitigation collar 160 is such that it allows the opening 122 to be placed in the eye at any location desired—in this case, the areosol mitigation collar 160 is between 10 mm to 30 mm in length. Such a length allows for the opening 122 to be moved in the eye while the areosol mitigation collar 160 is deformed. In this example, to allow for visualization of the eye during surgery, the areosol mitigation collar 160 is made of a clear material. In this example, To allow for proper deformation of areosol mitigation collar 160, the areosol mitigation collar 160 is made of a flexible material (such as silicone) that is easily deformed. In addition the contact surface 302 is a low friction material to allow for it to move along the surface of the eye as the areosol mitigation collar 160 is deformed. In one example, the areosol mitigation collar 160 is made of a hydrophilic material. Alternatively, or in addition, the proximal end of the areosol mitigation collar 160 at the connection to sleeve 162 moves along sleeve 100.

Figure 5A:
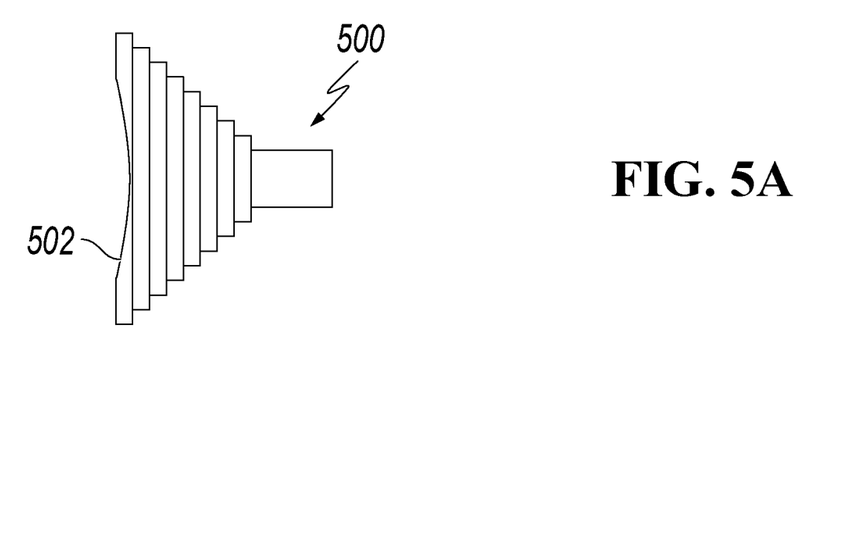
FIGS. 5A, 5B, 5C, and 5D are views of various embodiments of an aerosol mitigation collar according to aspects of the disclosure.
Figure 5B:
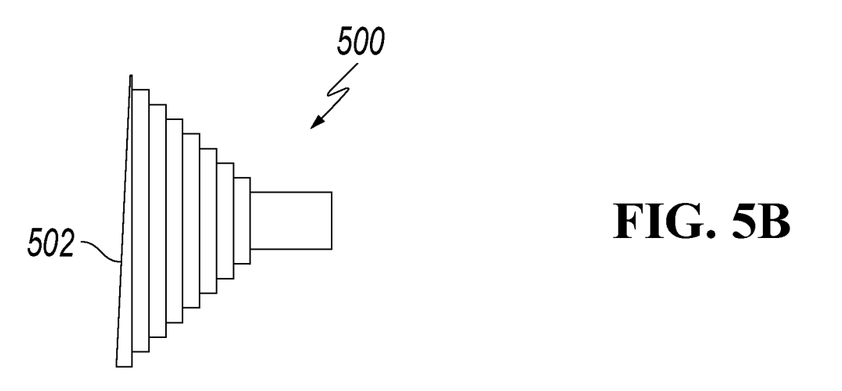
Figure 5C:
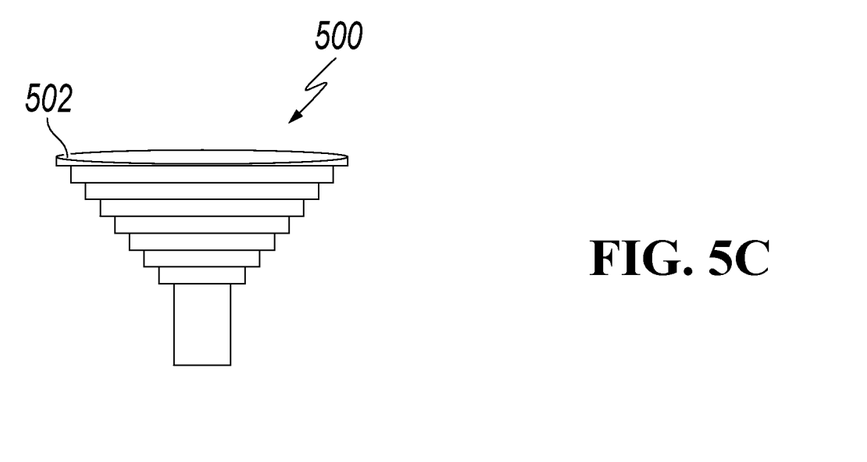
Figure 5D:
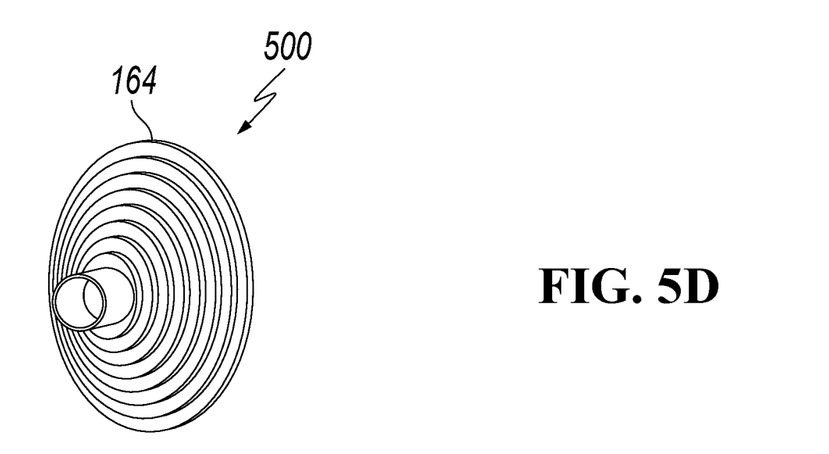

FIGS. 5A-5D are views of various embodiments of an aerosol mitigation collar 500. The aerosol mitigation collar 500 includes an asymmetrical contact surface 502. As shown in FIG. 5A, the contact surface 502 is contoured so as to accommodate contact with the limbus, conjunctiva, cornea, and other external structures of the eye 402. In various embodiments, the contact surface 502 may exhibit a smooth curvilinear shape. In other embodiments, as shown in FIGS. 5B-5C, the contact surface 502 may be angled from one side to the opposite side. Thus, as shown in FIGS. 5A and 5B, the aerosol mitigation collar 500 includes an asymmetrical longitudinal cross section. In various embodiments, a radial cross sectional shape of the skirt 164 may be generally circular. In other embodiments, as shown in FIG. 5D, the radial cross-sectional shape of the skirt 164 may be, for example, elliptical, oval, or teardrop shaped.

Figure 6:
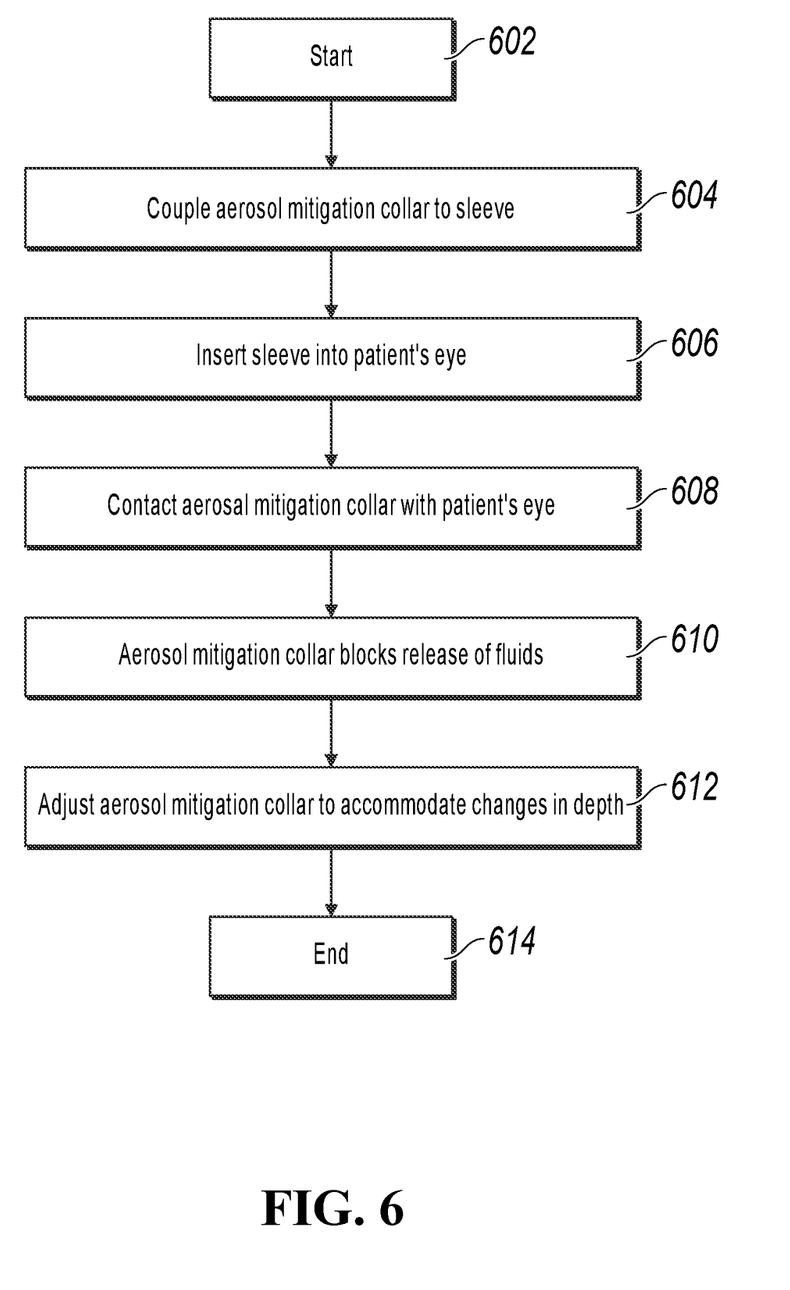
FIG. 6 is a flow diagram of a process for containing aerosol fluids during an ophthalmic procedure according to aspects of the disclosure.

FIG. 6 is a flow diagram illustrating a process 600 for containing aerosol fluids during an ophthalmic procedure. The process 600 begins at step 602. At step 604, the aerosol mitigation collar 160 is coupled to a sleeve 100. At step 606, the sleeve is inserted into an incision in a patient's eye. At step 608, a contact surface 302 of the aerosol mitigation collar 160 contacts the patient's eye. In various embodiments, the contact surface 302 may contact various external ophthalmic structures including, for example, the limbus, the conjunctiva, and the cornea. At step 610, the aerosol mitigation collar 160 blocks emission of aerosolized bodily fluids from the incision. At step 612, the aerosol mitigation collar 160 is adjusted to accommodate changes in depth of the sleeve 100. In various embodiments, the aerosol mitigation collar 160 may be adjusted, for example, through the expansion and compression of accordion-like pleats 166 formed in the skirt 164 of the aerosol mitigation collar 160. In such embodiments, the pleats 166 are compressed as the sleeve 100 is inserted deeper into the incision and the pleats 166 are expanded as the sleeve 100 is withdrawn from the incision. In other embodiments, the aerosol mitigation collar 160 is slidably disposed on the sleeve 100 such that, as the sleeve 100 in inserted deeper into the incision, the aerosol mitigation collar 160 slides proximally on the sleeve 100. Likewise, as the sleeve 100 is withdrawn from the incision, the aerosol mitigation collar slides distally on the sleeve 100. The process ends at step 614.

Figure 7A:
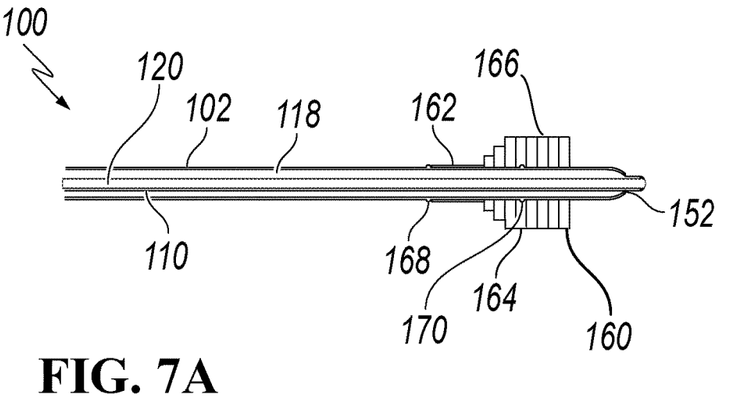
FIGS. 7A, 7B, 7C, and 7D are views of various embodiments of an aerosol mitigation collar according to aspects of the disclosure.
Figure 7B:
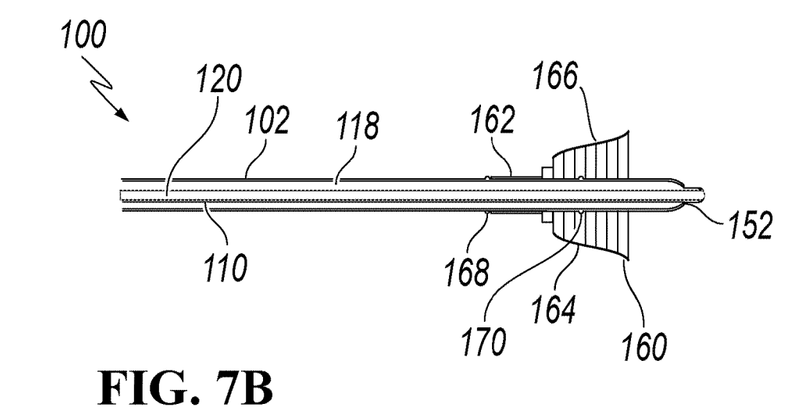
Figure 7C:
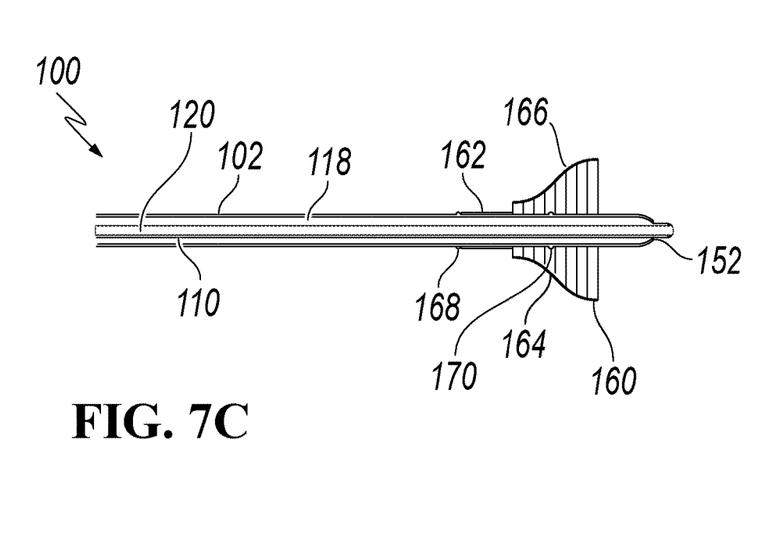
Figure 7D:
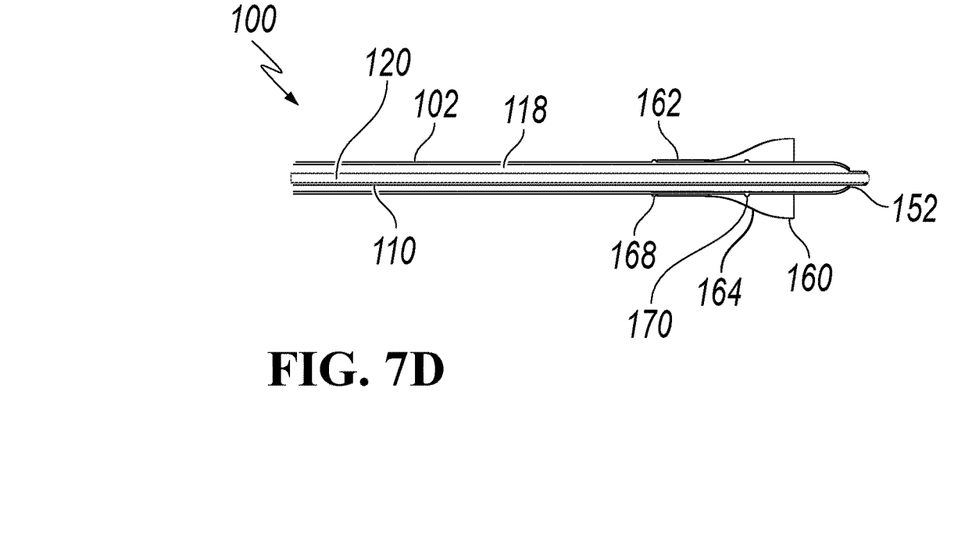

FIGS. 7A-7D show various embodiments of aerosol mitigation collar 160. In FIG. 7A, aerosol mitigation collar 160 is cylindrical in shape. Skirt 164 extends from sleeve 162 toward opening 152 at the distal end of the phacoemulsification needle. Skirt 164 has sidewalls that are parallel to instrument 110. Skirt 164 may be between 10 mm and 30 mm in length. In this example, aerosol mitigation collar 160 is made of a clear, flexible, low-friction material such as silicone. When opening 152 is located in the eye, aerosol mitigation collar 160 seals to the outside surface of the eye and can be resiliently deformed as the opening 152 of instrument 110 is moved in the eye. In FIG. 7B, aerosol mitigation collar 160 is bell-shaped. Skirt 164 extends from sleeve 162 toward opening 152 at the distal end of the phacoemulsification needle. Skirt 164 has sidewalls that curve outward from instrument 110 as shown. The distal end of skirt 164 flares outward slightly to provide a sealing surface that seals to the eye. Skirt 164 may be between 10 mm and 30 mm in length. In this example, aerosol mitigation collar 160 is made of a clear, flexible, low-friction material such as silicone. When opening 152 is located in the eye, aerosol mitigation collar 160 seals to the outside surface of the eye and can be resiliently deformed as the opening 152 of instrument 110 is moved in the eye. In FIG. 7C, aerosol mitigation collar 160 is bell-shaped. Skirt 164 extends from sleeve 162 toward opening 152 at the distal end of the phacoemulsification needle. Skirt 164 has sidewalls that curve outward from instrument 110 as shown. The distal end of skirt 164 flares inward slightly to provide a sealing surface that seals to the eye. Skirt 164 may be between 10 mm and 30 mm in length. In this example, aerosol mitigation collar 160 is made of a clear, flexible, low-friction material such as silicone. When opening 152 is located in the eye, aerosol mitigation collar 160 seals to the outside surface of the eye and can be resiliently deformed as the opening 152 of instrument 110 is moved in the eye. In FIG. 7D, aerosol mitigation collar 160 is bell-shaped. Skirt 164 extends from sleeve 162 toward opening 152 at the distal end of the phacoemulsification needle. Skirt 164 has sidewalls that curve outward slightly from instrument 110 as shown. The diameter of skirt 164 at its widest point is about 3 mm. Skirt 164 may be between 10 mm and 30 mm in length. In this example, aerosol mitigation collar 160 is made of a clear, flexible, low-friction material such as silicone. When opening 152 is located in the eye, aerosol mitigation collar 160 seals to the outside surface of the eye and can be resiliently deformed as the opening 152 of instrument 110 is moved in the eye. In FIGS. 7A-7D, pleats 166 are optional, and the widest diameter of aerosol mitigation collar 160 is between about 3 mm and 5 mm.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," "generally," and "about" may be substituted with "within [a percentage] of" what is specified.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. An ophthalmic surgical instrument system, comprising:
    an ophthalmic instrument having a shaft and a lumen extending through the shaft;
    a sleeve having a tubular body portion that receives and surrounds the ophthalmic instrument;
    an annulus defined between the ophthalmic instrument and the sleeve, wherein:
        the annulus provides a first conduit for irrigation flow towards a distal end of the sleeve when irrigation fluid is directed therethrough; and
        the lumen of the ophthalmic instrument provides a second conduit for aspiration flow away from the distal end of the sleeve when suction force is applied therethrough; and
    an aerosol mitigation collar extending from the sleeve, the aerosol mitigation collar comprising a tubular section and a skirt extending outwardly and distally from the tubular section such that a diameter of the skirt progressively increases from a proximal end of the skirt to a distal end of the skirt.

2. The ophthalmic surgical instrument system of claim 1, comprising a plurality of pleats formed in the skirt, wherein the plurality of pleats are configured to facilitate compression and expansion of the skirt so as to accommodate movement of the ophthalmic instrument within an eye.

3. The ophthalmic surgical instrument system of claim 2, wherein the skirt has at least one of a cone shape or a parabolic shape.

4. The ophthalmic surgical instrument system of claim 1, wherein the aerosol mitigation collar is integrally formed with the sleeve.

5. The ophthalmic surgical instrument system of claim 1, wherein the tubular section is slidably disposed around the sleeve.

6. The ophthalmic surgical instrument system of claim 5, wherein sliding movement of the aerosol mitigation collar relative to the sleeve is configured to accommodate movement of the ophthalmic instrument within an eye.

7. The ophthalmic surgical instrument system of claim 1, wherein the aerosol mitigation collar is configured to prevent release of aerosolized fluids from an eye.

8. The ophthalmic surgical instrument system of claim 1, wherein the aerosol mitigation collar comprises a symmetrical longitudinal cross section.

9. The ophthalmic surgical instrument system of claim 1, wherein the aerosol mitigation collar comprises an asymmetrical longitudinal cross section.

10. The ophthalmic surgical instrument system of claim 1, wherein the aerosol mitigation collar comprises a non-circular radial cross section.

11. An aerosol mitigation collar, comprising:
    a tubular section that receives a portion of a sleeve, the sleeve having therein:

a first conduit for irrigation flow towards a distal end thereof when irrigation fluid is directed therethrough; and a second conduit for aspiration away from the distal end thereof when suction force is applied therethrough;

a skirt extending outwardly and distally from the tubular section such that a diameter of the skirt progressively increases from a proximal end of the skirt to a distal end of the skirt;

a contact surface disposed at the distal end of the skirt; and a plurality of pleats formed in the skirt, the plurality of pleats configured to facilitate compression and expansion of the aerosol mitigation collar.

12. The aerosol mitigation collar of claim 11, wherein the aerosol mitigation collar is configured to prevent release of aerosolized fluids from an eye.

13. The aerosol mitigation collar of claim 11, wherein the aerosol mitigation collar comprises a symmetrical longitudinal cross section.

14. The aerosol mitigation collar of claim 11, wherein the aerosol mitigation collar comprises an asymmetrical longitudinal cross section.

15. The aerosol mitigation collar of claim 14, wherein the contact surface is contoured to facilitate contact with exterior structures of an eye.

16. The aerosol mitigation collar of claim 11, wherein the aerosol mitigation collar comprises a non-circular radial cross section.

17. The aerosol mitigation collar of claim 11, wherein the plurality of pleats are configured to facilitate compression and expansion of the skirt so as to accommodate movement of an ophthalmic instrument within an eye.

18. A method of containing aerosol fluids during ophthalmic procedures, the method comprising:

coupling an aerosol mitigation collar to a sleeve, the aerosol mitigation collar comprising a tubular section and a skirt extending outwardly and distally from the tubular section such that a diameter of the skirt progressively increases from a proximal end of the skirt to a distal end of the skirt;

contacting a contact surface of the aerosol mitigation collar with an exterior surface of an eye during an ophthalmic procedure;

directing, through a first conduit in the sleeve, irrigation fluid towards a distal end of the sleeve;

applying, through a second conduit in the sleeve, suction force away from the distal end of the sleeve; blocking, via the aerosol mitigation collar, release of aerosol fluids from the eye; and adjusting a depth of the sleeve within the eye while maintaining contact between the contact surface and the eye.

19. The method of claim 18, wherein maintaining contact between the contact surface and the eye comprises at least one of compressing and expanding a plurality of pleats formed in the aerosol mitigation collar.

20. The method of claim 18, wherein maintaining contact between the contact surface and the eye comprises sliding the aerosol mitigation collar along the sleeve.

* * * * *